US006451762B1

(12) United States Patent
Havelund et al.

(10) Patent No.: US 6,451,762 B1
(45) Date of Patent: Sep. 17, 2002

(54) AGGREGATES OF HUMAN INSULIN DERIVATIVES

(75) Inventors: Svend Havelund, Bagsværd (DK); Ib Jonassen, Valby (DK); Per Balschmidt, Espergærde (DK); Thomas Høeg-Jensen, Klampenborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/227,774

(22) Filed: Jan. 8, 1999

Related U.S. Application Data

(63) Continuation-in-part of application No. 09/193,552, filed on Nov. 17, 1998, which is a continuation of application No. PCT/DK98/00461, filed on Oct. 23, 1998.
(60) Provisional application No. 60/064,170, filed on Nov. 24, 1997.

(30) Foreign Application Priority Data

Oct. 24, 1997 (DK) .............................................. 1218/97

(51) Int. Cl.⁷ .......................... A61K 38/28; C07K 14/62
(52) U.S. Cl. ............................... 514/3; 514/4; 514/866; 530/303; 530/304
(58) Field of Search ............................... 514/3, 4, 866; 530/303, 304

(56) References Cited

U.S. PATENT DOCUMENTS 5,866,538 A * 2/1999 Norup et al. .................. 514/3
6,011,077 A * 1/2000 Havelund et al. .............. 514/3

FOREIGN PATENT DOCUMENTS

| WO | WO 91/12817 |   | 9/1991 |
| WO | WO95/07931  | * | 3/1995 |
| WO | WO 95/07931 |   | 3/1995 |
| WO | WO 96/00107 |   | 1/1996 |
| WO | WO 96/04307 |   | 2/1996 |
| WO | WO 97/31022 | * | 8/1997 |

OTHER PUBLICATIONS

Kurtzhals et al., (1996) J. of Pharmaceutical Sciences 85(3):304–308.
Sluzky et al., (1991) Proc. Nat. Acad. Sci. USA 88:9377–9381.
File medline on STN. No. 90282737. Rafter, G.W. Reaction of insulin with reduced gluthathione', Biochemistry International, vol. 20, No. 4, pp. 817–820. 1990 abstract only.*

Katakam et al., PDA Joournal of Pharmaceutical Science & Technology, vol. 49, No. 4, pp. 160–165 (1995).

Brange et al., Journal of Pharmaceutical Sciences, vol. 86, No. 5, pp. 517–525 (1997).

Samuel et al., Clin. exp. Immunol., vol. 33, pp. 252–260 (1978).

Kurtzhals et al., Journal of Pharmaceutical Sciences, vol. 85, No. 3, pp. 304–308 (1996).

Markussen et al., Diabetologia, vol. 39, pp. 281–288 (1996).

Kurtzhals et al., Biochem. J., vol. 312, pp. 725–731 (1995).

Eugéne Fredericq, Archives of Biochemistry and Biophysics, vol. 65, pp. 218–228 (1956).

Whittingham et al., Biochemistry, vol. 36, pp. 2826–2831 (1997).

Jeffrey et al., Nature, vol. 197, No. 4872, pp. 1104–1105 (1963).

Blundell et al., Diabetes 21 (Suppl. 2), pp. 492–505 (1972).

Grant et al., Biochem. J., vol. 126, pp. 433–440 (1972).

Jeffrey et al., Biochemistry, vol. 5, No. 12, pp. 3820–3824 (1996).

Jeffrey et al., Biochemistry, vol. 5, No. 2, pp. 489–498 (1966).

Blundell et al., Adv. Protein Chem., vol. 26, pp. 297–330 (1972).

Kurtz et al., Diabetologia, vol. 25, pp. 322–324 (1983).

* cited by examiner

Primary Examiner—Christopher S. F. Low
Assistant Examiner—Anish Gupta
(74) Attorney, Agent, or Firm—Reza Green, Esq.; Richard W. Bork, Esq.

(57) ABSTRACT

The present invention relates-to protracted acting, water-soluble aggregates of derivatives of human insulin, derivatives of human insulin capable of forming such aggregates, pharmaceutical compositions containing them, and to the use of such aggregates in the treatment of diabetes.

3 Claims, 4 Drawing Sheets

AGGREGATES OF HUMAN INSULIN DERIVATIVES

CROSS-REFERENCE TO RELATED APPLICATIONS

This application is a continuation-in-part of pending U.S. application Ser. No. 09/193,552 filed Nov. 17, 1998, which is a continuation of PCT/DK98/00461 filed Oct. 23, 1998 which claims priority under 35 U.S.C. 119 of Danish application 1218197 filed Oct. 24, 1997 and U.S. provisional application No. 60/064,170 filed Nov. 24, 1997, the contents of which are fully incorporated herein by reference.

FIELD OF THE INVENTION

The present invention relates to protracted acting, water-soluble aggregates of derivatives of human insulin, derivatives of human insulin capable of forming such aggregates, pharmaceutical compositions containing them, and to the use of such aggregates in the treatment of diabetes

BACKGROUND OF THE INVENTION

Diabetes is a general term for disorders in man having excessive urine excretion as in diabetes mellitus and diabetes insipidus. Diabetes mellitus is a metabolic disorder in which the ability to utilize glucose is more or less completely lost. About 2% of all people suffer from diabetes.

Since the introduction of insulin in the 1920's, continuous strides have been made to improve the treatment of diabetes mellitus. To help avoid extreme glycaemia levels, diabetic patients often practice multiple injection therapy, whereby insulin is administered with each meal. Many diabetic patients are treated with multiple daily insulin injections in a regimen comprising one or two dailyl injections of a protracted insulin to cover the basal requirement supplemented by bolus injections of a rapid acting insulin to cover the meal-related requirements.

Protracted insulin compositions are well known in the art. Thus, one main type of protracted insulin compositions comprises injectable aqueous suspensions of insulin crystals or amorphous insulin. In these compositions, the insulin compounds utilised typically are protamine insulin, zinc insulin or protamine zinc insulin.

When human or animal insulin is brought to form higher associated forms, e.g. in the presence of $Zn^{2+}$-ions, precipitation in the form of crystals or amorphous product is the result (Brange, Galenics of Insulin, pp. 120–27, Springer Verlag 1987). Thus, at pH 7 and using 6 $Zn^{2+}$/hexamer of porcine insulin the result is an almost complete precipitation from solution (Grant, Biochem J. 126, 433–440, 1972). The highest soluble aggregate suggested is composed of 4 hexameric units, corresponding to a molecular weight of about 144 kDa. Blundell et al. (Diabetes 21 (Suppl. 2), 492–505, 1972) describe the soluble unit of porcine insulin in the presence of $Zn^{2+}$ at pH 7 as a hexamer. Early ultracentrifugation studies at pH 2 showed the insulin dimer, Mw 12 kDa, to be the prevailing species (Jeffrey, Nature 197, 1104–1105, 1963; Jeffrey, Biochemistry 5, 489–498, 1966; Jeffrey, Biochemistry 5, 3820–3824, 1966). Fredericq, working at pH 8 and using 0.4–0.8% (w/w) $Zn^{2+}$ relative to insulin, reported a molecular weight of 72 kDa, corresponding to a dodecameric structure and, using 1% Zn, molecular weights of about 200–300 kDa (Arch. Biochem Biophys. 65, 218–28, 1956). A comprehensive review of the association states of animal insulin is found in Blundell et al. (Adv. Protein Chem. 26, 297–330, 1972).

Certain drawbacks are associated with the use of insulin suspensions. Thus, in order to secure an accurate dosing, the insulin particles must be suspended homogeneously by gentle shaking before a defined volume of the suspension is withdrawn from a vial or expelled from a cartridge. Also, for the sitorage of insulin suspensions, the temperature must be kept within more narrow limits than for insulin solutions in order to avoid lump formation or coagulation.

While it was earlier believed that protamines were non-immunogenic, it has now turned out that protamines can be immunogenic in man and that their use for medical purposes may lead to formation of antibodies (Samuel et al., Studies on the immunogenicity of protamines in humans and experimental animals by means of a micro-complement fixation test, Clin. Exp. Immunol. 33, pp. 252–260 (1978)).

Also, evidence has been found that the protamine-insulin complex is itself immunogenic (Kurtz et al., Circulating IgG antibody to protamine in patients treated with protamine-insulins. Diabetologica 25, pp. 322–324 (1983)). Therefore, with some patients the use of protracted insulin compositions containing protamines must be avoided.

Another type of protracted insulin compositions are solutions having a pH value below physiological pH from which the insulin will precipitate because of the rise in the pH value when the solution is injected. A drawback is that the solid particles of the insulin act as a local irritant causing inflammation of the tissue at the site of injection.

WO 91/12817 (Novo Nordisk A/S) discloses protracted, soluble insulin compositions comprising insulin complexes of cobalt(III). The protraction of these complexes is only intermediate and the bioavailability is reduced.

Soluble insulin derivatives containing lipophilic substituents linked to the ε-amino group of a lysine residue in any of the positions B26 to B30 have been described in e.g. WO 95/07931 (Novo Nordisk A/S), WO 96/60107 (Novo Nordisk A/S) and WO 97/31022 (Novo Nordisk A/S). Such derivatives have a protracted action after subcutaneous injection as compared to soluble human insulin, and this protracted action has been explained by a reversible binding to albumin in subcutis, blood and peripheral tissue (Markussen, Diabetologia 39, 281–288, 1996; Kurzhials, Biochem J. 312, 725–731, 1995; Kurzhals, J. Pharm Sciences 85, 304–308, 1996; and Whittingham, Biochemistry 36, 2826–2831, 1997).

However, we have now discovered a new mechanism of prolonging the action of some of the soluble insulin derivatives. The new mechanism is based on the partly or fully formation of soluble aggregated forms of the derivatives, featuring a size larger than aldolase (Mw=158 kDa) in a defined gel filtration system.

DESCRIPTION OF THE INVENTION

The expression "insulin derivative" as used herein (and related expressions) refers to human insulin or an analogue thereof in which at least one organic substituent is bound to one or more of the amino acids. Preferably, the insulin derivative contains only one lipophilic substituent.

By "analogue of human insulin" as used herein (and related expressions) is meant human insulin in which one or more amino acids have been deleted and/or replaced by other amino acids, including non-codeable amino acids, or human insulin comprising additional amino acids, i.e. more than 51 amino acids. Preferably, the analogue of human insulin contains only substitutions. In another preferred embodiment, the total number of different amino acids between the analogue of human insulin and human insulin does not exceed six, preferably is five, more preferably is four, even more preferably is three, even more preferably is two, and most preferably is one.

The present invention is based on the discovery of a new aggregated and soluble form of insulin derivatives. The new, soluble aggregated form of insulin derivatives dissociates slowly after subcutaneous injection, making them suitable for a long-acting insulin preparation, the advantage being that the preparation contains no precipitate. The advantages of soluble rather than suspension preparations are higher precision in dosing, avoidance of shaking of the vial or pen, allowance for a thinner needle meaning less pain during injection, easier filling of vials or cartridge and avoidance of a ball in the cartridge used to suspend the precipitate in the absence of air.

More specifically, the present invention relates to a water-soluble aggregate of insulin derivatives, characterised by having a size larger than aldolase, preferably larger than ferritin, as determined by a gel filtration system as specified herein.

The aggregate according to the invention preferably has an apparent volume corresponding to a $K_{AV}$ value of less than 0.32, preferably less filtration using a Sephacryl® S-300 HR gel, or a $K_{AV}$ value of less than 0.50, preferably less than 0.40, as determined by gel filtration using a Superose® 6HR gel.

The aggregate is preferably soluble at a pH in the range of 6.8 to 8.5.

The new aggregated form can be observed for insulin derivatives under conditions where the hexameric unit is known to exist for most insulins. Thus, in a preferred embodiment, the aggregated form is composed of hexameric subunits, preferably of at least 4, more preferably 5 to 50, still more preferably 5 to 200, hexameric subunits. Any hexameric subunit of the aggregated forms of this invention may have any of the known $R_6$, $R_3T_3$, or $T_6$ structures (Kaarsholm, Biochemistry 28, 4427–4435, 1989).

Figure 2:
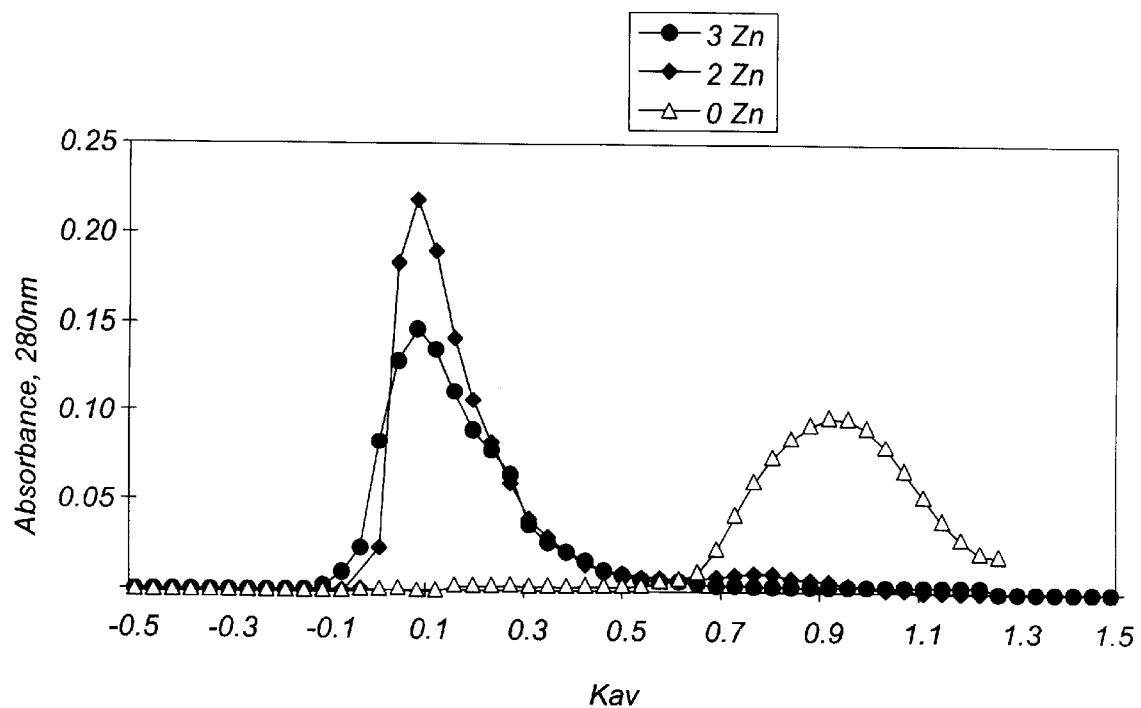
FIG. 2. Gel filtration of $Lys^{B29}(N^{\epsilon}\omega$-carboxyheptadecanoyl) des(B30) human insulin having 0, 2 and 3 $Zn^{2+}$/hexamer, respectively, using a column of Sephacryl® S-300 HR in an aqueous neutral eluent comprising 1,25 mM sodium chloride and 20 mM sodium phosphate at pH 7.4, demonstrating the importance of $Zn^{2+}$ for the formation of aggregates for this derivative. A column of 28×1 cm is eluted at a rate of 15 ml/h. Insulin derivatives were injected (200 μl) as a standard preparation comprising 600 FM derivative, 0, 2 or 3 $Zn^{2+}$/6 molecules of insulin, 20 mM NaCl, 16 mM phenol, 16 mM m-cresol, 7 mM sodium phosphate at pH 7.5.

Substances like $Zn^{2+}$ and phenolic compounds known to stabilise the hexameric unit are also found to stabilise the new aggregated form of some insulin derivatives. The building blocks forming the aggregates may be the hexameric units known from the X-ray crystallographic determined structure of insulin (Blundell, Diabetes 21 (Suppl. 2), 492–505, 1972). Ions like $Zn^{2+}$, known to stabilise the hexameric unit as 2 or 4 $Zn^{2+}$/hexamer complexes (Blundell, Diabetes 21 (Suppl. 2), 492–505, 1972), are essential for the formation of aggregates for some derivatives, like for $Lys^{B29}$ ($N^\epsilon\omega$-carboxyheptadecanoyl) des(B30) human insulin. FIG. 2 shows gel filtration of $Lys^{B29}(N^{68}$ ω-carboxyheptadecanoyl) des(B30) human insulin in the system described herein of preparations containing 0, 2, and 3 $Zn^{2+}$/hexamer, respectively. In the absence of $Zn^{2+}$ aggregates are not formed, the elution position indicating the presence of a monomer or dimer. Thus, the aggregate according to invention preferably comprises at least 2 zinc ions, more preferably 2 to 5 zinc ions, still more preferably 2 to 3 zinc ions, per 6 molecules of insulin derivative. Moreover, the aggregate advantageously comprises at least 3 molecules of a phenolic compound per 6 molecules of insulin derivative. In the central cavity of the 2 $Zn^{2+}$/hexamer structure 6 residues of $Glu^{B13}$ provide binding sites for up to 3 $Ca^{2+}$ ions (Sudmeier et al., Science 212, 560–562, 1981). Thus, addition of $Ca^{2+}$ ions stabilises the hexamer and may be added to the pharmaceutical formulations, on the condition that the insulin derivative remains in solution.

The disappearance half-time of the aggregate of the invention after subcutaneous injection in humans is preferably as long as or longer than that of a human insulin NPH preparation.

In a particularly preferred embodiment of the present invention, the aggregate is composed of insulin derivatives which have an albumin binding which is lower than that of $Lys^{B29}(N^\epsilon$tetradecanoyl) des(B30) human insulin.

The preferred primary structures of insulin derivatives to be employed in the present invention are those in which:

a) the residues B24-B30 of the B-chain of the insulin derivative is the sequence Phe-X-X-X-X-X-X, where each X independently represents any codable amino acid or a deletion;

b) the residues B25-B30 of the B-chain of the insulin derivative is the sequence Phe-X-X-X-X-X, where each X independently represents any codable amino acid or a deletion;

c) the residues B26-B30 of the B-chain of the insulin derivative is the sequence Tyr-X-X-X-X, where each X independently represents any codable amino acid or a deletion;

d) the residues B27-B30 of the B-chain of the insulin derivative is the sequence Thr-X-X-X, where each X independently represents any codable amino acid or a deletion;

e) the residues B28-B30 of the B-chain of the insulin derivative is the sequence Pro-X-X, where each X independently represents any codable amino acid or a deletion; or f) the residues B29-B30 of the B-chain of the insulin derivative is the sequence Lys-X, where X represents any codable amino acid or a deletion;

provided that the insulin derivative exhibits a potency of at least 5%, e.g. as assessed by the free fat cell assay or by affinity to the insulin receptor.

In a preferred embodiment, each X mentioned above is independently is selected from the following group of amino acids: Phe, Tyr, Thr, Ser, Pro, Lys, Gly, Ala, Glu, Asp, Gln, His or is deleted. More preferably:

X in position B25 is selected from the following group of amino acids: Tyr, Phe, His, Gly or is deleted.

X in position B26 is selected from the following group of amino acids: Thr, Ala, Phe, Tyr or is deleted.

X in position B27 is selected from the following group of amino acids: Glu, Gln, Lys, Pro, Gly, Ala, Ser, Thr or is deleted.

X in position B28 is selected from the following group of amino acids: Asp, Glu, Gly, Ala, Lys, Pro or is deleted.

X in position B29 is selected from the following group of amino acids: Asp, Glu, Gly, Ala, Pro, Thr, Lys or is deleted.

X in position B30 is selected from the following group of amino acids: Lys, Ala, Ser, Thr or is deleted.

the amino acid in each of the positions A1-A20, B4-B12, and B14-B24 is the corresponding amino acid in human insulin, i.e., A1 is Gly, A2 is Ile, A3 is Val, A4 is Glu, A5 is Gln, A6 is Cys, A7 is Cys, A8 is Thr, A9 is Ser, A10 is Ile, A11 is Cys, A12 is Ser, A13 is Leu, A14 is Tyr, A15 is Gln, A16 is Leu, A17 is Glu, A18 is Asn, A19 is Tyr, A20 is Cys, B4 is Gln, B5 is His, B6 is Leu, B7 is Cys, B8 is Gly, B9 is Ser, B10 is His, B11 is Leu, B12 is Val, B14 is Ala, B15 is Leu, B16 is Tyr, B17 is Leu, B18 is Val, B19 is Cys, B20 is Gly, B21 is Glu, B22 is Arg, B23 is Gly, and B24 is Phe.

The insulin derivative can also contain other amino acid substitutions, particularly in the following positions: A21, B1, B2, B3 and B13.

The amino acid in position A21 is preferably selected from group consisting of Ala, Asn, Gln, Glu, Gly and Ser.

The amino acid in position B1 is preferably selected from Asp, Thr, Asn, Ser, Pro, Gln, Gly, Phe or is deleted.

The amino acid in position B2 is preferably selected from Glu, Pro, Asp, Ala and Val.

The amino acid in position B3 is preferably selected from the group consisting of Asn, Gln, Glu, Asp, Ala and Thr.

The amino acid in position B13 is preferably Glu or Gln.

The substituent at the lysine residue of the insulin derivative of the aggregate according to the invention is preferably a lipophilic group containing from 6 to 40 carbon atoms. More preferred are substituents which are acyl groups having from 6 to 40, preferably 12 to 36, carbon atoms.

The most preferred lipophilic substituents in the form of acyl groups are the following: $CH_3-(CH_2)_n-CO-$, $(COOH)-(CH_2)_n-CO-$, $(NH_2-CO)-(CH_2)_n-CO-$, $HO-(CH_2)_n-CO-$, where $4<n<38$.

In another preferred embodiment the lipophilic substituent is 5-α lithocholic acid or 5-β lithocholic acid.

In another preferred embodiment the lipophilic substituent is 5-α or 5-α isomers of cholic acid, hyocholic acid, deoxycholic acid, chenodeoxycholic acid, ursodeoxycholic acid, hyodeoxycholic acid or cholanic acid.

In another preferred embodiment the lipophilic substituent is fusidic acid, a fusidic acid derivative or glycyrrhetinic acid.

In yet another preferred embodiment the lipophilic substituent is connected to a lysine residue using an amino acid linker. According to this embodiment the lipophilic substituent is advantageously connected to a lysine residue via a γ- or an α-glutamyl linker, or via a β-or an α-aspartyl linker, or via an α-amido-γ-glutamyl linker, or via an α-amido-β-aspartyl linker.

The present invention furthermore provides novel insulin derivatives capable of forming aggregates. These insulin derivatives may be provided in the form of aggregates in pharmaceutical preparations or, alternatively, they may be provided in a non-aggregated form in pharmaceutical preparations, in which case the aggregates form after subcutaneous injection of said preparations.

Accordingly, the present invention furthermore is concerned with pharmaceutical preparations comprising an aggregate of insulin derivatives or non-aggregated insulin derivatives which form aggregates after subcutaneous injection.

Preferably, the pharmaceutical preparation according to the present invention comprises aggregates, a substantial fraction of which (preferably more than 75%) has a larger size than aldolase as determined by gel filtration using the medium of the preparation as eluent.

In another embodiment, a pharmaceutical preparation comprising both aggregating and rapid acting insulin analogues, the latter preferably being human insulin or one of the insulin analogues $Asp^{B28}$ human insulin, $Lys^{B28}Pro^{B29}$ human insulin or des(B30) human insulin, is provided. Such a preparation will provide both a rapid onset of action as well as a prolonged action profile.

In this embodiment, the pharmaceutical preparation preferably comprises aggregating insulin and rapid acting insulin in a molar ratio of 90:10 to 10:90.

The slow dissociation of the aggregated forms may be further slowed down in vivo by the addition of physiological acceptable agents that increase the viscosity of the pharmaceutical preparation. Thus, the pharmaceutical preparation according to the invention may furthermore comprise an agent which increases the viscosity, preferably polyethylene glycol, polypropylene glycol, copolymers thereof, dextrans and/or polylactides.

The pharmaceutical preparation preferably further comprises a buffer substance, such as a TRIS, phosphate, glycine or glycylglycine (or another zwitterionic substance) buffer, an isotonicity agent, such as NaCl, glycerol, mannitol and/or lactose, and phenol and/or m-cresol as preservatives. Among the auxiliary substances of a pharmaceutical preparation the sodium chloride, used as isotonic agent, and the phenol, used for preservation, are particular important by promoting the aggregation in the preparation and thereby effectively prolong the time of disappearance from the site of injection. The pharmaceutical preparation according to the invention preferably comprises $Na^+$ ions in a concentration of 10 to 150 mM.

The most preferred pharmaceutical preparation is a preparation containing 0.1–2 mM of an insulin derivative according to the present invention, 0.3–0.9% Zn (w/w relative to insulin derivative), and phenolic compounds like phenol or m-cresol or mixtures hereof in a total concentration of 5–50 mM, and $Na^+$ ions in a concentration of 10 mM to 150 mM The present invention furthermore relates to a method of treating diabetes mellitus comprising administering to a person in need of such treatment an effective amount of water-soluble aggregates of insulin derivatives according to the invention or effective amount an insulin derivative according to the invention, capable of forming water-soluble aggregates upon subcutaneous injection.

Figure 4:
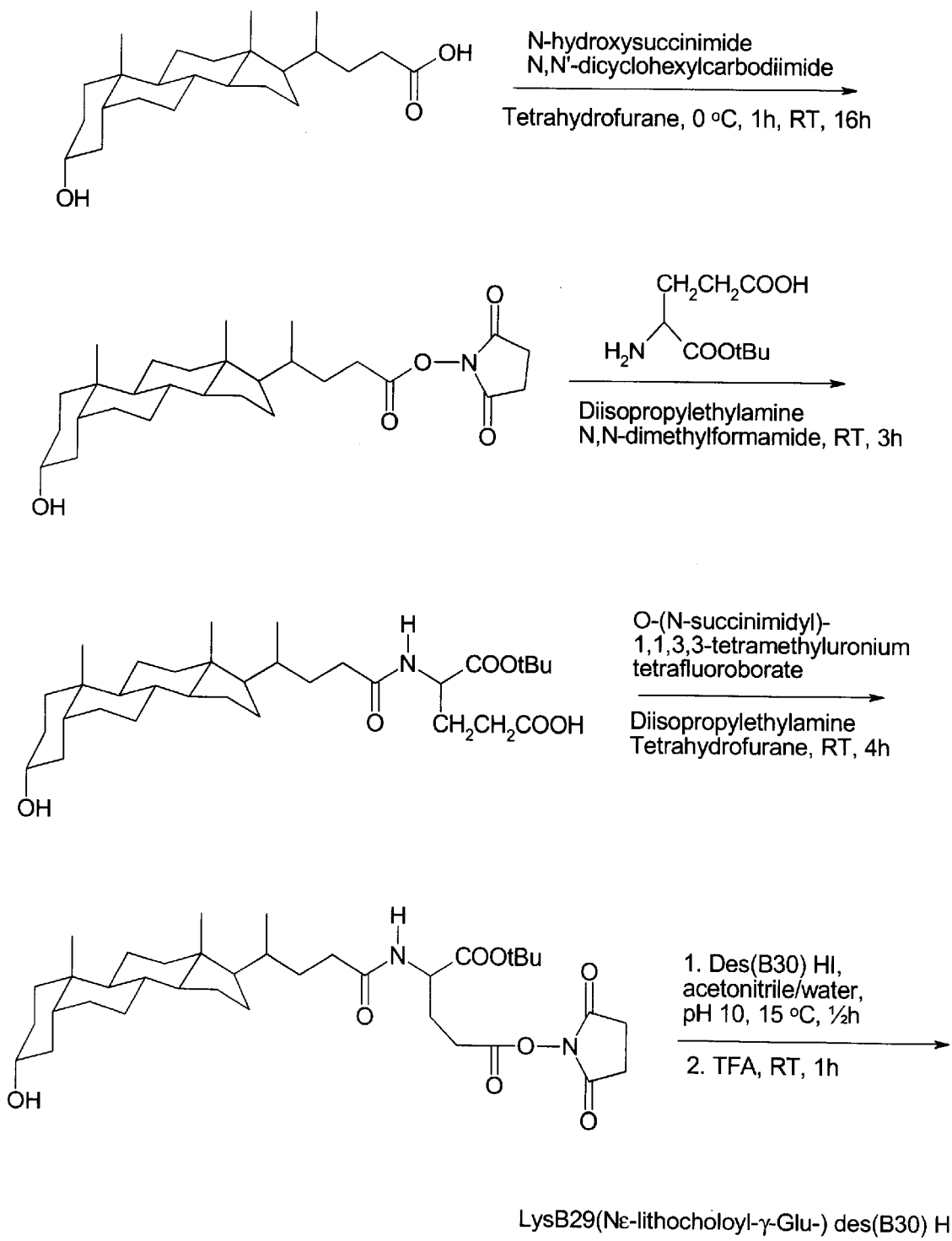
FIG. 4. Scheme of the synthesis of the conjugated ligands.

The insulin derivatives of the invention can be prepared by the general methods disclosed in WO 95/07931 (Novo Nordisk A/S), WO 96/00107 (Novo Nordisk A/S), WO 97/31022 (Novo Nordisk A/S), PCT application No. DK97/00296 (Novo Nordisk A/S), EP 511 600 (Kurakay Co. Ltd.) and EP 712 862 (Eli Lilly). The derivatives listed in Table 2 have been prepared by selective acylation of the ε-amino group of Lys$^{B29}$ of des(B30) human insulin by the ligands activated in the form of the respective N-hydroxysuccinimide esters. The conjugated ligands can be prepared using conventional peptide chemistry (FIG. 4).

Some of the derivatives listed in the aforementioned patent applications, and described in the publications of Markussen, Diabetologia 39, 281–288, 1996; Kurzhals, Biochem J. 312, 725–731, 1995; Kurzhals, J. Pharm Sciences 85, 304–308, 1996; and Whittingham, Biochemistry 36, 2826–2831, 1997 as being protracted due to the albumin binding mechanism, do also posses the ability to form high molecular weight soluble aggregates in accordance with the present invention. Ly B$^{29}$(N$^\epsilon$lithocholyl-γ-Glu-) des(B30) human insulin from WO 95/07931 and Ly$^{B29}$(N$^\epsilon$ω-carboxyheptadecanoyl-) des(B30) human insulin from WO 97/31022 are examples of insulin derivatives capable of forming high molecular weight soluble aggregates at neutral pH. There is selectivity between the lipophillic substituents in their ability to induce formation of aggregates. Thus, of the two isomers, Lys$^{B29}$(N$^\epsilon$lithocholyl-γ-Glu-) des(B30) human insulin and Lys$^{B29}$(N$^\epsilon$lithocholyl-α-Glu-) des(B30) human insulin, only the first forms aggregates in the formulation used, see Table 1.

Determination of Aggregate Formation

The aggregated form is demonstrated by gel filtration using a gel with an exclusion limit of 1,500 kDa for globular proteins and 400 kDa for linear dextrans. A pH neutral aqueous buffer system is used in the gel filtration and the insulin derivatives in the aggregated state are applied to the column in the form of a pharmaceutical preparation at a concentration of 600 nmol insulin/ml. The aggregated states of the insulin derivatives elute before aldolase, which has a molecular weight of 158 kDa.

The gel filtration experiment using the conditions prescribed in this section is the direct physico-chemical method to reveal the potential aggregate formation property of an insulin derivative. Disappearance after subcutaneous injection in pigs reflects the combination of the albumin binding and polymer formation properties of the insulin derivative, besides a variety of biological factors.

The formation of high molecular weight soluble aggregates is demonstrated by gel filtration using a column of Sephacryl® S-300 HR in an aqueous neutral eluent comprising 125 mM sodium chloride and 20 mM sodium phosphate at pH 7.4. This buffer system was chosen to mimic the ionic strength and pH of the tissue, in order to be able to detect derivatives aggregated under conditions similar to those after the subcutaneous injection. Obviously, in other buffer systems having lower concentration of sodium chloride or a lower or higher pH value the derivatives may not appear in the aggregated state. However, when the actual state of aggregation in a pharmaceutical preparation is to be assessed, the medium of the preparation, exclusive the Zn$^{2+}$ which is insulin bound, is used as the eluent for the gel filtration.

A column of 28×1 cm is eluted at a rate of 15 ml/h. Insulin derivatives were injected (200 μl) as a standard formulation comprising 600 μM derivative, 200 or 300 μM Zn$^{2+}$, 20 mM NaCl (or varied), 16 mM phenol, 16 mM m-cresol, 7 mM sodium phosphate at pH 7.5.

Figure 1:
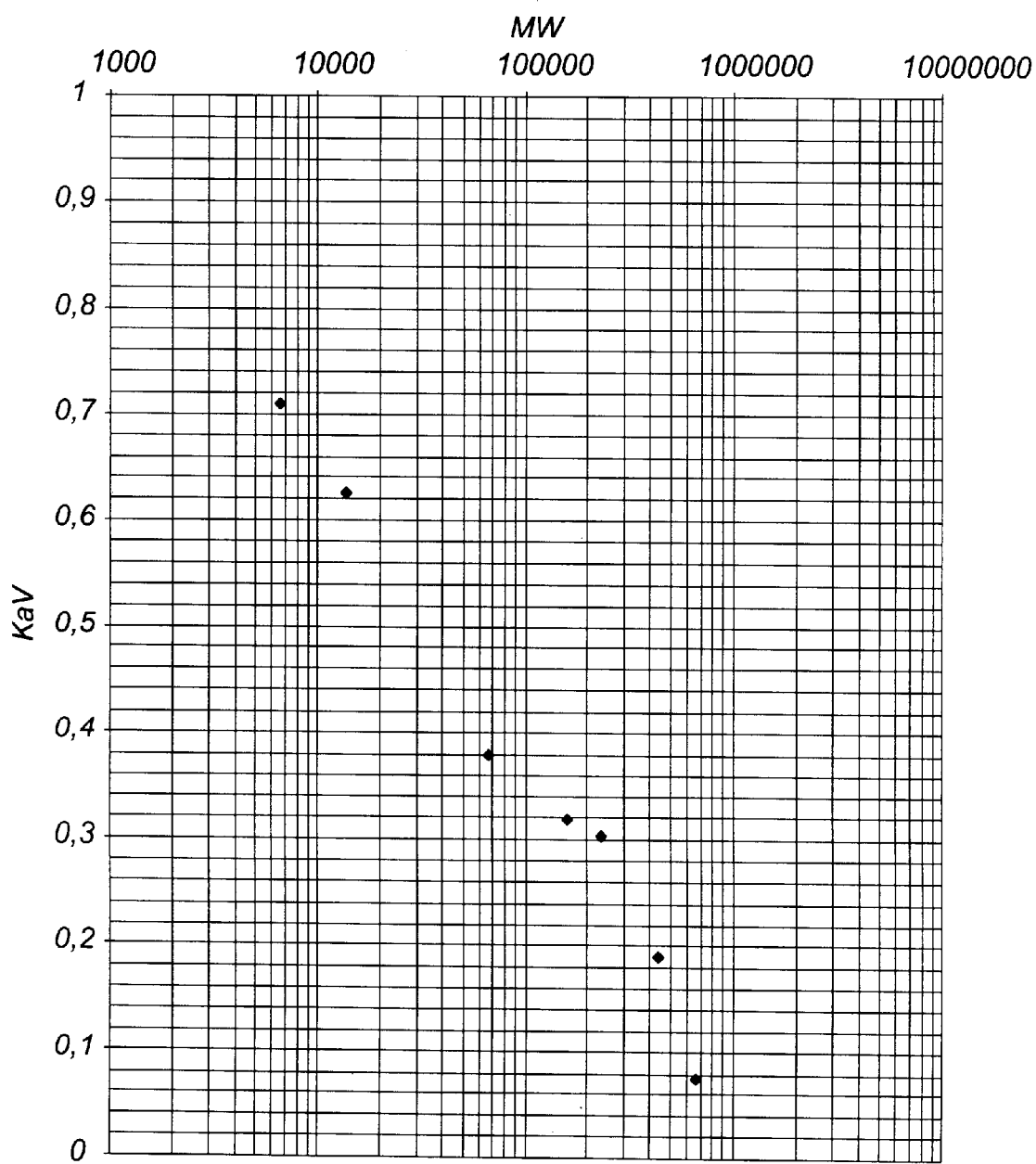
FIG. 1. Calibration curve of $K_{AV}$ values[ v]ersus molecular weight in the gel filtration system using a column of Sephacryl® S-300 HR in an aqueous neutral eluent comprising 125 mM sodium chloride and 20 mM sodium phosphate at pH 7.4. A near linear relation between $K_{AV}$ and the logarithm of the molecular weight is apparent. The standards are shown in Table 1.

Exclusion limit of Sephacryl® S-300 HR is stated by the manufacturer, Pharmacia, as a molecular weight of 1,500 kDa for globular proteins and 400 kDa for linear dextrans. In practice the elution of solutes of different size is characterised by the available volume as $K_{AV}$ values:

$$K_{AV} = (V_E - V_0)/(V_T - V_0)$$

where $V_E$ is elution volume, $V_0$ is void volume, e.g. elution volume of blue dextran, $V_T$ is total volume. Thus, the $K_{AV}$ value is independent of column dimension. In this system aldolase (Mw 158 kDa) elutes at about a $K_{AV}$ of 0.32, albumin (Mw of 67 kDa) at about a $K_{AV}$ of 0.38, and the monomeric form of insulin (Mw of 6 kDa) with a $K_{AV}$ of about 0.71. The calibration of the column using a series of molecular weight standards shows a near linear relation between $K_{AV}$ and the logarithm of the molecular weight, see FIG. 1. TABLE 1.

$K_{AV}$ values, albumin binding constants and disappearance half-times for associating insulin derivatives larger than aldolase (Mw 158 kDa), non-associating insulin derivatives smaller than aldolase and standards used as markers of molecular size. Albumin binding constants and disappearance half times in pigs have been normalised using Lys$^{B29}$ (N$^\epsilon$tetradecanoyl) des(B30) human insulin as the reference compound. Disappearance T$_{50\%}$ for NPH insulin in pigs have been measured to 10.5 h (Markussen et al. 1996).

| Compounds | $K_{AV}$ | Albumin binding $K_{ass}$, (mol/l)$^{-1}$ | Disappearance $T_{50\%}$ h |
|---|---|---|---|
| Associating derivatives of human insulin forming aggregates larger than aldolase.** | | | |
| Lys$^{B29}$(N$^\epsilon$ lithocholyl-γ-Glu-) des(B30) | 0.04* | 0.3 × 10$^5$ | 22.8 |
| Lys$^{B29}$(N$^\epsilon$ ω-carboxyheptadecanoyl) des(B30) | 0.05 | 25 × 10$^5$ | 18.7 |
| Lys$^{B29}$(N$^\epsilon$ ω-carboxynonadecanoyl) des(B30) | 0.04 | 36 × 10$^5$ | 21.9 |
| Lys$^{B29}$(N$^\epsilon$ cholesteryloxycarbonyl) | 0.00 | | |
| Non-associating derivatives of human insulin forming aggregates smaller than aldolase.** | | | |
| Human insulin*** | 0.61 | 0 | (2) |
| Human insulin (Zinc free) | 0.72 | | |
| Lys$^{B29}$(N$^\epsilon$ lithocholyl (Zinc free) | 0.74 | | |
| Lys$^{B29}$(N$^\epsilon$ decanoyl)*** | 0.67 | 0.06 × 10$^5$ | 5.1 |
| Lys$^{B29}$(N$^\epsilon$ tetradecanoyl) des(B30) | 0.51 | 1.0 × 10$^5$ | 14.3 |
| Lys$^{B29}$(N$^\epsilon$lithocholyl-α-Glu-) des(B30) | 0.53 | 0.3 × 10$^5$ | 11.8 |
| Standards.**** | | | |
| B9Asp, B27Glu human insulin (monomeric, Mw 6 kDa) | 0.71 | 0 | (1) |
| Ribonuclease (Mw 13.7 kDa) | 0.63 | | |
| Albumin (Mw 67 kDa) | 0.38 | | |
| Aldolase (Mw 158 kDa) | 0.32 | | |
| Catalase (Mw 232 kDa) | 0.30 | | |
| Ferritin (Mw 440 kDa) | 0.19 | | |
| Thyroglobulin (Mw 669 kDa) | 0.08 | | |

*75% of the derivatives eluted in the main peak, and 25% in the position of the monomer or dimer.
**Applied 200 μl sample as a pharmaceutical preparation comprising 600 μM of derivative, 200 μM Zn$^{2+}$, 0–20 mM sodium chloride, 7 mM sodium phosphate, 16 mM phenol, 16 mM m-cresol, 1.6% glycerol and pH of 7.5.
*Same as  but 300 μM Zn$^{2+}$.
****Standards applied dissolved in water.

Examples of insulin derivatives capable of forming soluble high molecular weight aggregates and having a protracted action based primarily on this property are Lys$^{B29}$ (N$^\epsilon$lithocholyl-γ-Glu-) des(B30) human insulin, see Table 1. Notably, the ratio between disappearance half time and albumin binding constant is high for this class of compounds. Examples of insulin derivatives incapable of forming soluble high molecular weight aggregates but having a protracted action based on the albumin binding property are $Lys^{B29}(N^\epsilon lithocholyl-\alpha-Glu-)$ des(B30) human insulin and $Lys^{B29}$ ($N^\epsilon$-tetradecanoyl-) des(B30) human insulin, see Table 1. Notably, the ratio between disappearance half time/albumin binding constant is low for this class of compounds.

Figure 3:
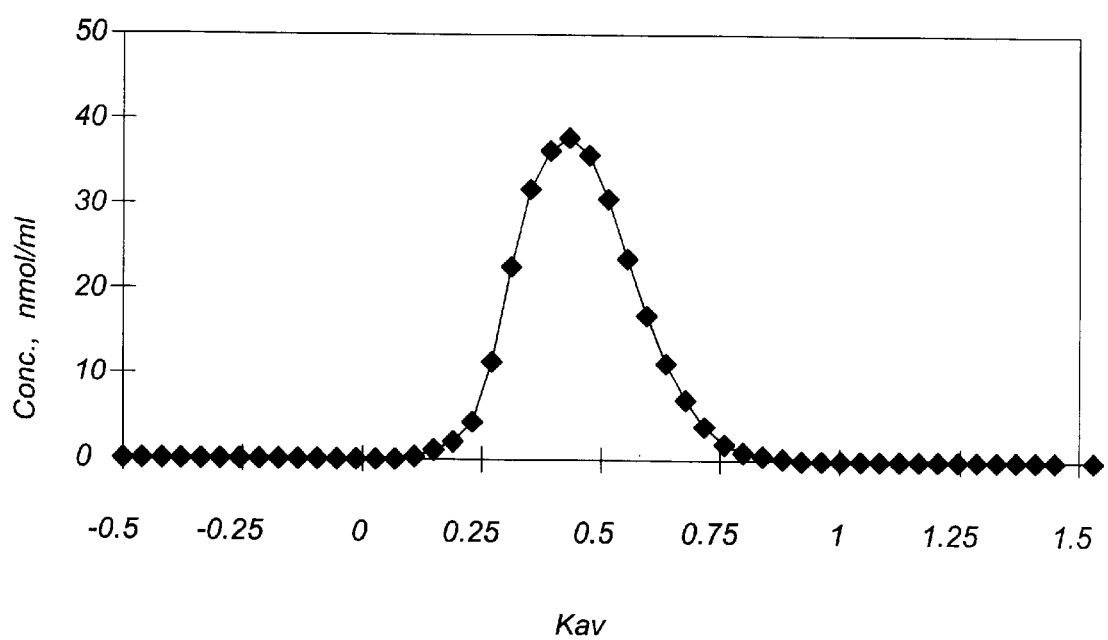
FIG. 3. Gel filtration of $Lys^{B29}(N^\epsilon\omega$-carboxyheptadecanoyl) des(B30) human insulin having 3 $Zn^{2+}$/hexamer using a column of Sephacryl® S-300 HR in an aqueous neutral eluent comprising 5 mM sodium phosphate buffer pH 7.5, 10 mM sodium chloride, 16 mM phenol, 16 mM m-cresol and 1.6% (w/v) glycerol. A comparison to FIG. 2 elucidates the importance of the sodium chloride concentration for the formation of aggregates of this derivative.

In WO 97/31022 a pharmaceutical preparation of $Lys^{B29}$ ($N^\epsilon$-(-carboxyheptadecanoyl) des(B30) human insulin has been formulated comprising 600 nmol/ml of derivative, 5 mM sodium phosphate buffer pH 7.5, 10 mM sodium chloride, 16 mM phenol, 16 mM m-cresol, 2–3 $Zn^{2+}$/hexamer and 1.6%(w/v) glycerol. In order to establish the degree of aggregation in this formulation a gel filtration was performed using the same column as described above but using the medium of the preparation as the eluent. The $Zn^{2+}$ is mostly insulin bound and is therefore not considered a constituent of the medium. Since the eluent contains phenolic substances the concentration of derivative in the fractions is monitored by HPLC, see FIG. 3. The $K_{AV}$ value of about 0.45 indicates that hexameric or dodecameric units are the prevailing species in the preparation, i.e. no high molecular weight aggregates of insulin derivatives was present in this published formulation.

An alternative method to measure the capability of insulin derivatives of forming soluble high molecular weight aggregates was developed, suitable for HPLC equipment. The column dimensions, injection volume, and flow rate correspond to the first method, whereas the temperature is increased to 37° C. and the phosphate buffer is changed to trishydroxymethylaminomethan hydrochloride and additional sodium chloride. The aggregated state of insulin is defined to elute before the gel filtration standard aldolase like in the first method.

$K_{AV}$-values are shown for two levels of zinc in Table 2. Compared to the reference, $Lys^{B29}(N^\epsilon tetradecanoyl-)$ des(B30) insulin, a long disappearance time from a subcutaneous depot is correlated with a tendency of the insulin derivative to form large aggregates.

TABLE 2

Aggregate formation of insulin derivatives measured by gel filtration method 2.

| Compounds | $K_{AV}$ (Superose 6HR)[2] | | Albumin binding | Disappearance in pigs[1], |
|---|---|---|---|---|
| | $2Zn^{2+}$/ 6 ins | $3Zn^{2+}$/ 6 ins | $K_{ass}$, ($10^5 M^{-1}$) | $T_{50\%}$, (h) |
| $Lys^{B29}(N^\epsilon$-lithocholoyl-$\gamma$-Glu-) des(B30) HI | 0.00 | −0.01 | 0.33 | 22.8 |
| $Lys^{B29}(N^\epsilon$-deoxycholoyl-$\gamma$-Glu-) des(B30) HI | 0.20 | 0.07 | 0.03 | 13.9 |
| $Lys^{B29}(N^\epsilon$-lithocholoyl-$\alpha$-amido-$\gamma$-Glu-) des(B30) HI | −0.02 | 0.00 | 0.23 | >34 |
| $Lys^{B29}(N^\epsilon$-lithocholoyl-$\beta$-Asp-) des(B30) HI | 0.18 | 0.11 | n.d. | n.d. |
| $Lys^{B29}(N^\epsilon$-lithocholoyl-$\beta$-Ala-) des(B30) HI | 0.00 | 0.13 | n.d. | n.d. |
| $Lys^{B29}(N^\epsilon$-lithocholoyl-$\gamma$-aminobutanoyl-) des(B30) HI | 0.06 | 0.00 | n.d. | n.d. |
| $Lys^{B29}(N^\epsilon$-lithocholoyl-) des(B30) HI | −0.01 | 0.23 | 0.38 | >34 |

TABLE 2-continued

Aggregate formation of insulin derivatives measured by gel filtration method 2.

| Compounds | $K_{AV}$ (Superose 6HR)[2] | | Albumin binding | Disappearance in pigs[1], |
|---|---|---|---|---|
| | $2Zn^{2+}$/ 6 ins | $3Zn^{2+}$/ 6 ins | $K_{ass}$, ($10^5 M^{-1}$) | $T_{50\%}$, (h) |
| $Lys^{B29}(N^\epsilon$-dehydrolithocholoyl-) des(B30) HI | 0.05 | 0.03 | 0.26 | >34 |
| $Lys^{B29}(N^\epsilon$-cholanoyl-) des(B30) HI | 0.40 | 0.17 | 0.48 | 20.1 |
| $Lys^{B29}(N^\epsilon$-hexadecanoyl-$\alpha$-amido-$\gamma$-Glu-) des(B30) HI | 0.38 | 0.41 | 0.56 | 15.3 |
| $Asp^{A21} Lys^{B29}(N^\epsilon$-tetradecanoyl-) des(B30) HI | 0.55 | 0.46 | 0.97 | 16.4 |
| $Lys^{B29}(N^\epsilon$-tetradecanoyl-) des(B30) HI | 0.58 | 0.56 | 1.00 | 14.3 |
| Human insulin, (HI) | 0.64 | 0.64 | — | 2 |
| Standards: | | | | |
| $Asp^{B9} Glu^{B27}$ HI (monomeric, Mw 6 kDa) | 0.73 | | | |
| Ribonuclease (Mw 13.7 kDa) | 0.72 | | | |
| Ovalbumin (Mw 43 kDa) | 0.58 | | | |
| Aldolase (Mw 158 kDa) | 0.50 | | | |
| Ferritin (Mw 440 kDa) | 0.40 | | | |
| Thyroglobulin (Mw 669 kDa) | 0.28 | | | |

[1]Normalised to $Lys^{B29}(N^\epsilon$ tetradecanoyl-) des(B30) human insulin ($T_{50\%}$ = 14.3 h)
[2]Superose 6 HR 10/30 (Pharmacia Biotech) is eluted at 37° C. by sodium chloride 140 mM, trishydroxymethylaminomethan 10 mM, sodium azide 0.02%, and hydrochloric acid added to pH 7.4. A run time time of 90 min. (0.25 ml/min.) is followed by a washing period of 150 min. (0.5 ml/min.). The injection volume was 200 μl.

What is claimed is:

1. A water-soluble aggregate of an insulin derivative having a lipophilic group, wherein the aggregate (a) has a size larger than aldolase, (b) comprises 2 to 5 zinc ions per 6 molecules of insulin derivative, and (c) is formed in an environment having an ionic strength and pH of the tissue after subcutaneous injection, wherein the insulin derivative is $Lys^{B29}(N^\epsilon cholesteryloxycarbonyl)$ human insulin.

2. A water-soluble aggregate of an insulin derivative having a lipophilic group containing from 12 to 36 carbon atoms, wherein the aggregate (a) has a size larger than aldolase, (b) comprises 2 to 5 zinc ions per 6 molecules of insulin derivative, and (c) is formed in an environment having an ionic strength and pH of the tissue after subcutaneous injection, wherein the lipophilic substituent is fusidic acid, a fusidic acid derivative or glycyrrhetinic acid.

3. A water-soluble aggregate of an insulin derivative having a lipophilic group containing from 12 to 36 carbon atoms, wherein the aggregate (a) has a size larger than aldolase, (b) comprises 2 to 5 zinc ions per 6 molecules of insulin derivative, and (c) is formed in an environment having an ionic strength and pH of the tissue after subcutaneous injection, wherein an acyl group is linked to a lysine residue using an amino acid as linker.

* * * * *

UNITED STATES PATENT AND TRADEMARK OFFICE
CERTIFICATE OF CORRECTION

PATENT NO. : 6,451,762 B1
APPLICATION NO. : 09/227774
DATED : September 17, 2002
INVENTOR(S) : Havelund et al.

It is certified that error appears in the above-identified patent and that said Letters Patent is hereby corrected as shown below:

Title page item (60), Related US Application Data - Change "Provisional application No. 60/064,170, filed on Nov. 24, 1997." to --Provisional application No. 60/064,170, filed on Nov. 4, 1997.--

On the title page item (57), Abstract, line 1 - Change "relates-to" to --relates to--

Column 1, line 11 – Change "Danish application 1218197" to --Danish application 1218/97--

Column 1, line 35 - Change "two dailyl injections" to --two daily injections--

Column 2, line 6 - Change "sitorage of" to --storage of--

Column 2, line 54 - Change "values[ v]ersus" to --values versus--

Column 3, line 3 - Change "600 FM derivative" to --600 µM derivative--

Column 3, line 56 – Change "less filtration" to --less than 0.20, as deteremined by gel, filtration--

Column 5, line 23 – Change "Gin" to --Gln--

Column 7, line 14 – Change "Ly B$^{29}$" to --Lys$^{B29}$--

Column 7, line 15 – Change "Ly$^{b29}$" to --Lys$^{b29}$--

UNITED STATES PATENT AND TRADEMARK OFFICE
CERTIFICATE OF CORRECTION

PATENT NO. : 6,451,762 B1
APPLICATION NO. : 09/227774
DATED : September 17, 2002
INVENTOR(S) : Havelund et al.

It is certified that error appears in the above-identified patent and that said Letters Patent is hereby corrected as shown below:

Column 8, line 1 – 4 – Change "$_{AV} = (V_o^E )/( V_o^T$" to --$K_{av} = (V_e - V_o)/(V_T - V_o)$--

Signed and Sealed this

Twenty-first Day of August, 2007

JON W. DUDAS
*Director of the United States Patent and Trademark Office*